United States Patent [19]

Thompson

[11] Patent Number: 4,591,523

[45] Date of Patent: May 27, 1986

[54] APERTURED MACROSCOPICALLY EXPANDED THREE-DIMENSIONAL POLYMERIC WEB EXHIBITING BREATHEABILITY AND RESISTANCE TO FLUID TRANSMISSION

[75] Inventor: Hugh A. Thompson, Fairfield, Ohio

[73] Assignee: The Procter & Gamble Company, Cincinnati, Ohio

[21] Appl. No.: 740,112

[22] Filed: May 31, 1985

[51] Int. Cl.$^4$ .............................................. B32B 3/00
[52] U.S. Cl. ......................... 428/131; 428/137; 428/138; 428/141; 428/284; 428/286; 428/913; 604/358
[58] Field of Search ............... 604/358; 428/131, 137, 428/138, 141, 284, 286, 913

[56] References Cited

U.S. PATENT DOCUMENTS

| | | | |
|---|---|---|---|
| D. 278,468 | 4/1985 | Trotman et al. | D92/1.1 |
| 810,120 | 1/1906 | Green | 128/284 |
| 2,273,542 | 2/1942 | Tasker | 128/284 |
| 3,156,242 | 11/1964 | Crowe, Jr. | 128/296 |
| 3,292,619 | 12/1966 | Egler | 128/156 |
| 3,371,667 | 3/1968 | Morse | 128/290 |
| 3,426,754 | 2/1969 | Bierenbaum et al. | 128/156 |
| 3,559,648 | 2/1971 | Mason, Jr. | 128/287 |
| 3,814,101 | 6/1974 | Kozak | 128/287 |
| 3,929,135 | 12/1975 | Thompson | 128/287 |
| 3,957,414 | 5/1976 | Bussey, Jr. et al. | 425/384 |
| 3,965,906 | 6/1976 | Karami | 128/287 |
| 3,966,383 | 6/1976 | Bussey, Jr. et al. | 425/388 |
| 3,979,494 | 9/1976 | Ericson | 264/154 |
| 3,989,867 | 11/1976 | Sisson | 428/132 |
| 3,994,299 | 11/1976 | Karami | 128/287 |
| 4,041,951 | 8/1977 | Sanford | 128/287 |

(List continued on next page.)

FOREIGN PATENT DOCUMENTS

| | | |
|---|---|---|
| 101082A | 2/1984 | European Pat. Off. . |
| 845826 | 8/1960 | United Kingdom . |
| 1160625 | 8/1969 | United Kingdom . |
| 2021479 | 12/1979 | United Kingdom . |
| 2103933 | 3/1983 | United Kingdom . |

OTHER PUBLICATIONS

Commonly assigned, copending patent application Ser. No. 623,274, filed on Jun. 21, 1984 in the name of Thomas Ward Osborne, III and entitled, Sanitary Napkin with Gross Foramina Overlying a Low Density, Resilient Structure.

Primary Examiner—James J. Bell
Attorney, Agent, or Firm—E. Kelly Linman; John V. Gorman; Richard C. Witte

[57] ABSTRACT

The present invention pertains, in a particularly preferred embodiment, to an apertured, macroscopically expanded, resilient three-dimensional polymeric web which is believed to have particular utility as a breatheable barrier for a disposable bandage such as a diaper. The web preferably comprises a deeply drawn three-dimensional structure containing a multiplicity of debossments of macroscopic (i.e., visibly perceivable by the normal human eye at a perpendicular distance of about one foot) cross-section, each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. The smaller apertures in each end wall are so spaced relative to all adjacent apertures in the end wall that the aqueous fluid menisci supported in the apertures do not contact one another or the side wall. In a disposable absorbent bandage context, the second surface of the web containing the end walls with small apertures therein is placed in contact with the absorbent core portion of the bandage and the surface of the web in which the debossments originate is oriented so as to contact the wearer's outer garments in use.

12 Claims, 8 Drawing Figures

U.S. PATENT DOCUMENTS

| | | | |
|---|---|---|---|
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,226,828 | 10/1980 | Hall | 264/555 |
| 4,248,822 | 2/1981 | Schmidt | 264/154 |
| 4,321,924 | 3/1982 | Ahr | 128/287 |
| 4,323,069 | 4/1982 | Ahr et al. | 128/287 |
| 4,327,730 | 5/1982 | Sorensen | 128/287 |
| 4,341,216 | 7/1982 | Obenour | 128/287 |
| 4,341,217 | 7/1982 | Ferguson et al. | 128/290 |
| 4,342,314 | 8/1982 | Radel et al. | 128/287 |
| 4,343,848 | 8/1982 | Leonard, Jr. | 428/156 |
| 4,351,784 | 9/1982 | Thomas et al. | 264/22 |
| 4,395,215 | 7/1983 | Bishop | 425/290 |
| 4,397,644 | 8/1983 | Matthews et al. | 604/378 |
| 4,463,045 | 7/1984 | Ahr et al. | 428/131 |
| 4,477,502 | 10/1984 | O'Sullivan | 428/35 |
| 4,508,256 | 4/1985 | Radel et al. | 228/152 |
| 4,509,908 | 4/1985 | Mullane, Jr. | 425/290 |
| 4,518,643 | 5/1985 | Francis | 428/131 |

4,591,523

APERTURED MACROSCOPICALLY EXPANDED THREE-DIMENSIONAL POLYMERIC WEB EXHIBITING BREATHEABILITY AND RESISTANCE TO FLUID TRANSMISSION

TECHNICAL FIELD

The present invention relates to an apertured, macroscopically expanded, resilient, three-dimensional polymeric web which is breatheable, but which is resistant to the transmission of aqueous fluid.

The present invention has further relation to a polymeric web which is deeply drawn to form a resilient, three-dimensional structure containing a multiplicity of debossments of macroscopic cross-section, each of said debossments originating as an aperture in a first surface of the web and having a continuously interconnected side wall extending in the direction of a second, remotely located, parallel surface of the web. The side wall terminates to form an end wall in the second surface of the web. The end wall includes a multiplicity of smaller apertures, each of the smaller apertures being sized and shaped so as to independently support an aqueous fluid meniscus. The smaller apertures are so spaced relative to all adjacent apertures in the end wall and to the side wall of the debossment that the aqueous fluid menisci supported in the apertures do not contact one another.

The present invention has further relation to such a web which exhibits sufficient resistance to compression that the first and second surfaces of the web do not normally become coplanar with one another when subjected to compressive loadings in use. If the web is employed in applications such as a breatheable back sheet for a disposable diaper, this is estimated to be less than about one pound per square inch for a baby in sitting position. By preventing the second surface of the web and the first surface of the web from becoming coplanar, contact between the wearer's outer garments and the aqueous fluid menisci supported in the apertures of the end walls of the debossments is normally prevented. Prevention of contact normally prevents transfer of the aqueous fluid to the wearer's outer garments.

The present invention has still further relation to such a web which exhibits a degree of resilience sufficient to repeatedly return to its substantially undeformed condition when the in use compressive loads are removed from the structure.

Finally, the present invention has particular relation to an absorbent bandage structure, wherein the second surface of a polymeric web of the present invention is placed in contact with the absorbent core portion of the bandage and the first surface of the web is placed so as to contact the wearer's outer garments in use.

BACKGROUND ART

Disposable absorptive devices such as disposable diapers, sanitary napkins, disposable bedpads, incontinent briefs, and the like are well known. It most instances, these structures function as a disposable bandage to absorb liquid from the human body and retain that liquid. It is also known to cover the exterior of these devices with a flexible, plastic sheet to prevent the liquid absorbent from striking through the absorptive device and soiling outer wearing apparel. The waterproof, plastic sheet of the prior art does prevent strikethrough and helps contain the liquid within the device. However, it precludes a self drying of the absorptive device by evaporation of the fluid contained therein. Accordingly, it is desirable to utilize a breatheable backsheet, particularly in absorptive devices which are worn for an extended period of time. It is also desirable, in such circumstances, to shield the liquid in the absorbent body from adjacent clothing.

Suggestions for permeable backsheets have been made in the art with the purpose of allowing some circulation of air between the interior of the absorptive device and the surrounding atmosphere. U.S. Pat. No. 2,570,011, issued to Stamberger on Oct. 2, 1951, approaches the problem of providing a breatheable backsheet for absorptive devices by teaching a diaper having both absorbent and retarding sections. The retarding section is a chemically treated portion of a cloth diaper and is folded toward the outside thereof. This retarding section is treated to prevent penetration of urine. U.S. Pat. No. 3,156,242, issued to Crowe, Jr., on Nov. 10, 1964, teaches an absorbent device having an absorbent body covered by a non-absorbent, flexible film. The film is air pervious so as to permit drying of the absorbent body held thereunder. The air perviousness of the film is achieved by using a microporous film or a film having holes or slits therein. U.S. Pat. No. 2,027,810, issued to Cooper on Jan. 14, 1936, teaches a film having apertured bosses therein which is designed to be liquid pervious. Additional prior art structures employing porous thermoplastic webs associated with an absorbent body are disclosed in the following references: U.S. Pat. No. 3,292,619, issued to Egler on Dec. 20, 1966; U.S. Pat. No. 3,426,754, issued to Bierenbaum et al. on Feb. 11, 1969; and U.S. Pat. No. 3,446,208, issued to Fukuda on May 27, 1969.

Still another absorptive device having a breatheable backsheet resistant to aqueous fluid passage is disclosed in commonly assigned U.S. Pat. No. 3,989,867 issued to Sisson on Nov. 2, 1976, said patent being hereby incorporated herein by reference. The backsheet employed in the absorptive device of Sisson has a plurality of bosses therein, each boss having an aperture which forms a pore in the backsheet. In the preferred embodiment shown in FIGS. 3 and 4, the bosses are grouped in patterns and each pattern forms an embossed area. The bosses are conical and have an included angle, denoted by $a$, of between about 30° and 135°, preferably between about 60° and 100°. The angle provides thickness to the backsheet and also provides a boss which will collapse, i.e., the opposite walls will come together, when pressure is exerted on the diaper in use. According to the teachings of Sisson, heat and vapors can escape through the apertures, but the movement of fluid therethrough is substantially prevented, even if the fluid is under a slight pressure. According to Sisson, the apertures should be substantially uniformly distributed over the area of the backsheet through which transmission is desired and the open area of the backsheet should be in the range of about $\frac{1}{2}$% to about 10% of the available area of the backsheet, most preferably in the range of from about 1% to about 5% of the available area of the backsheet. According to the teachings of Sisson, the embossed, aperture backsheet is most effective when the bosses are pointed toward the absorbent body rather than away from the absorbent body.

Still another material suggested for use as a breatheable backsheet in a disposable diaper is the resilient plastic web disclosed in commonly assigned U.S. Pat. No. 4,342,314 issued to Radel et al. on Aug. 3, 1982, said patent being hereby incorporated herein by reference. The Radel et al. patent discloses a resilient plastic web exhibiting a combination of fiber-like and plastic properties. In a particularly preferred embodiment, the web exhibits a fine-scale, three-dimensional microstructure comprising a regulated continuum of capillary networks of steadily decreasing size originating in and extending from a first surface of the web and terminating to form apertures in a second remotely located surface of the web. While a primary purpose of the web is to promote rapid fluid transport from the first surface of the web to its second surface, it is also suggested that the web might be employed as a breatheable backsheet resistant to aqueous liquid passage by orienting the web so as to place the second surface of the web extending the smaller openings in contact with the absorbent pad of the diaper and the first surface of the web exhibiting the larger openings adjacent the wearer's apparel. Webs of this basic type are generally shown in FIGS. 6, 6A, 6B and 7 of the Radel et al. patent.

Despite the beneficial characteristics exhibited by webs of the type disclosed in the aforementioned commonly assigned patents to Sisson and Radel et al., absorptive devices employing such webs as breatheable members have not met with widespread commercial acceptance.

Accordingly, it is a principal object of the present invention to provide an apertured, macroscopically expanded, three-dimensional polymer web exhibiting an improvement ability to transmit vapor, yet which is resistant to aqueous fluid transfer.

It is another object of the present invention to provide a macroscopically expanded, three-dimensional polymeric web of the aforementioned type which is particularly well suited for use as a breatheable back sheet in an absorptive device.

It is another object of the present invention to provide such a three-dimensional web having sufficient overall caliper and resistance to compression that the opposed surfaces of the web do not normally become coplanar under compressive loadings typically experienced in a disposable absorbent bandage.

DISCLOSURE OF THE INVENTION

The present invention pertains, in a particularly preferred embodiment, to an apertured, macroscopically expanded, resilient three-dimensional polymeric web which is believed to have particular utility as a breatheable barrier for a disposable bandage such as a diaper. The web preferably comprises a deeply drawn three-dimensional structure containing a multiplicity of debossments of macroscopic (i.e., visibly perceivable by the normal human eye at a perpendicular distance of about one foot) cross-section, each of said debossments originating as an aperture in a first surface of the web and having a continuously interconnected side wall extending in the direction of a second, remotely located parallel surface of the web. The side wall of each debossment terminates to form an end wall in the second surface of the web. The end wall includes a multiplicity of apertures, each of said apertures being sized and shaped to independently support an aqueous fluid meniscus. The smaller apertures in each end wall are so spaced relative to all adjacent apertures in the end wall that the aqueous fluid menisci supported in the apertures do not contact one another. In a particularly preferred embodiment, the aqueous fluid menisci also do not contact the side wall of the debossment.

To prevent the aqueous fluid menisci supported in the apertures from contacting the wearer's outer garments when the web is used as a breatheable backsheet for an absorbent bandage, it is necessary that the web exhibit sufficient resistance to compression that the first and second surfaces of the web do not normally become coplanar with one another when subjected to typical compressive loads by the wearer's body. (This is estimated to be less than about one pound per square inch for a baby in sitting position.) The web also preferably exhibits a degree of resilience sufficient to return substantially to its undeformed condition when the compressive loads are removed from the structure. In a disposable absorbent bandage context, the second surface of the web containing the end walls with small apertures therein is placed in contact with the absorbent core portion of the bandage and the surface of the web in which the debossments originate is oriented so as to contact the wearer's outer garments in use.

Preferred methods and apparatus for forming said apertured, macroscopically expanded, breatheable three-dimensional polymeric webs are also disclosed.

BRIEF DESCRIPTION OF THE DRAWINGS

While the specification concludes with claims particularly pointing out and distinctly claiming the present invention, it is believed the present invention will be better understood from the following description in which:

DETAILED DESCRIPTION OF THE INVENTION

While the present invention will be described in the context of providing an apertured, macroscopically expanded, three-dimensional, resilient polymeric web for use as a breathable backsheet on an absorbent bandage such as a disposable diaper, the present invention is in no way limited to such application. The present invention may in fact be practiced to great advantage in many situations where it is desired to pass fluid vapor through the web, yet resist the transmission of aqueous liquid to surfaces which come in contact with the web. The detailed description contained herein, which relates to a preferred structure and its use as a breathable backsheet in a disposable diaper, will allow one skilled in the art to readily adapt the invention to other devices.

Figure 1:
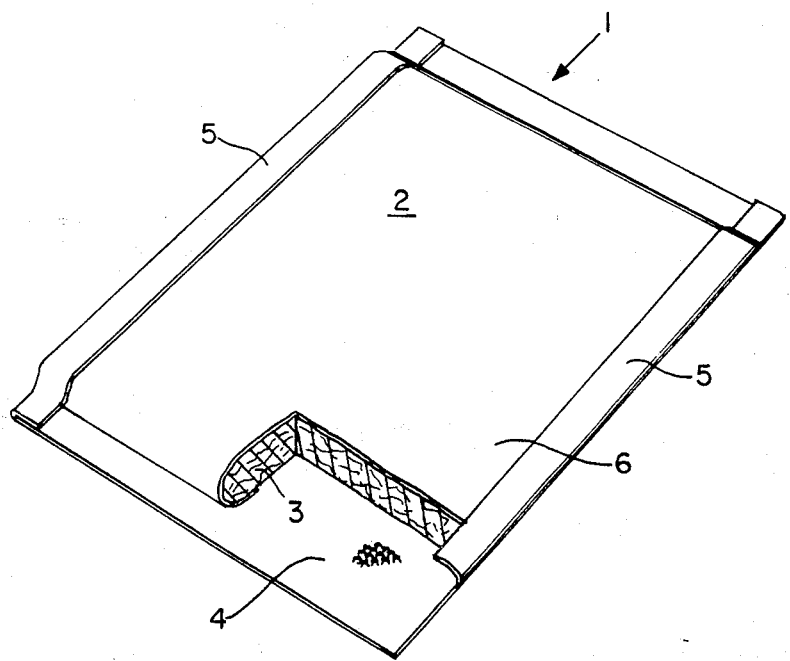
FIG. 1 is a simplified perspective representation of an unfolded disposable diaper employing a web of the present invention as a breathable backsheet, said diaper having portions of its components cut away for clarity.

FIG. 1 is a perspective view of a disposable absorbent bandage comprising a diaper in an unfolded condition. Various layers have been cut away to more clearly show the structural details of this embodiment. The disposable diaper is referred to generally by the reference numeral 1. A fluid-pervious topsheet which may be comprised of materials well known in the art, e.g., non-wovens, apertured plastics, etc., is shown at 2. The other major components of the disposable diaper 1 are the absorbent element or pad 3 and the backsheet 4 comprised of a web of the present invention. In general, the side flaps 5 of the backsheet 4 are folded so as to cover the edges of the absorbent pad 3 and topsheet 2. Topsheet 2 is generally folded to completely enclose the ends of the absorbent pad 3. The drawing of diaper 1 in FIG. 1 is a simplified representation of a disposable diaper. A more detailed description of a preferred embodiment of a disposable diaper is contained in commonly assigned U.S. Pat. No. 3,952,745, issued to Duncan on Apr. 27, 1976, said patent being hereby incorporated herein by reference.

As will be appreciated by those skilled in the art, the precise performance parameters for the disposable absorbent bandage generally shown in FIG. 1 will depend upon the use to which the structure is to be put. In general, the greater the volume of fluid material discharged into the absorbent bandage 1, the greater will be the need for breatheability in the backsheet 4.

Figure 2:
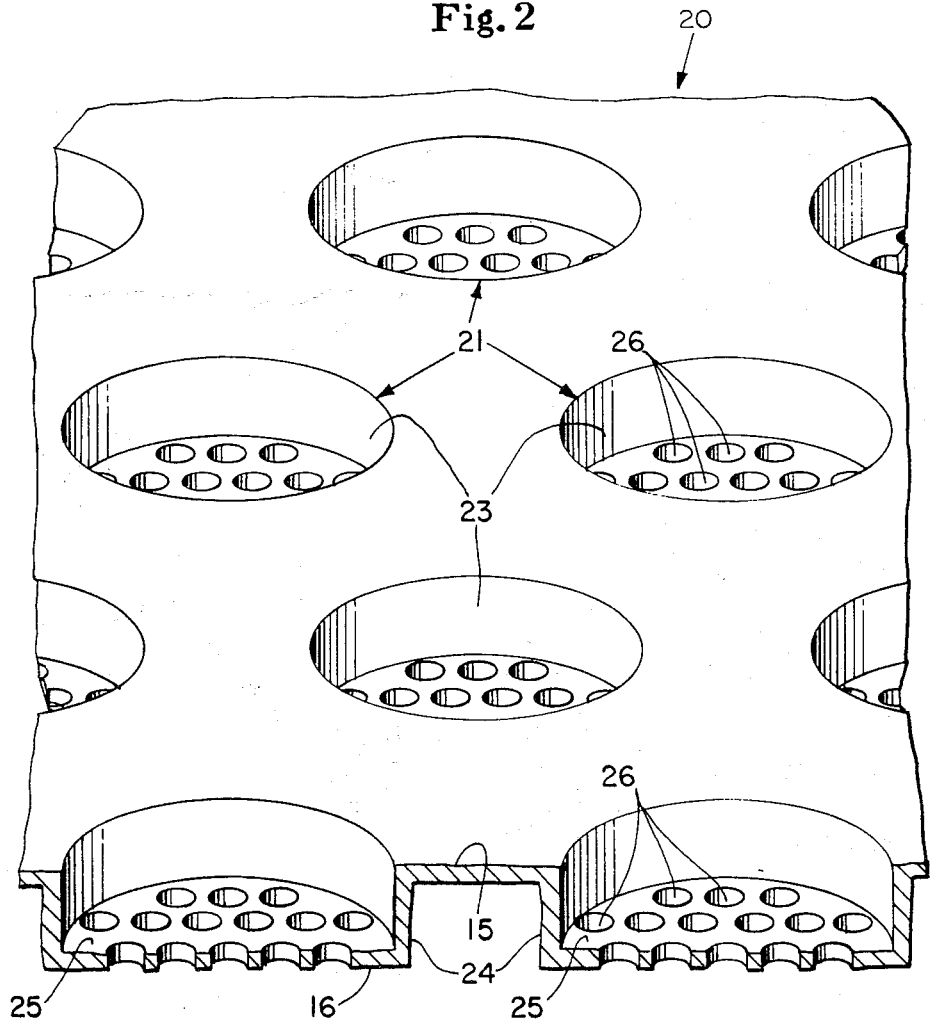
FIG. 2 is a greatly enlarged, simplified perspective illustration of a segment of an apertured, macroscopically expanded three-dimensional polymeric web suitable for use as a backsheet in a disposable diaper such as that shown in FIG. 1.

FIG. 2 discloses a particularly preferred apertured macroscopically expanded, three-dimensional polymeric web 20 of the present invention. Web 20 is particularly suitable as a starting material for backsheet 4 in a disposable diaper such as that illustrated in FIG. 1.

Macroscopically expanded, three-dimensional polymeric web 20 exhibits a multiplicity of cylindrical capillary networks 21 which, when viewed from overhead, are of macroscopic cross-section, i.e., they are visually perceivable by the normal human eye at a perpendicular distance of about one foot. As can be seen in FIG. 2, macroscopic cross-section debossments 21 are of a common size. This is not a requirement of the present invention. Indeed, it is feasible to employ macroscopic cross-section debossments of differing size to provide enhanced pattern flexibility, improved aesthetics, or to comply with specific functional parameters required by the product in which the breatheable web is employed.

As can be seen in FIG. 2, each macroscopic cross-section debossment 21 originates as an aperture 23 in the first surface 15 of the web 20. A continuously interconnected side wall 24 places each aperture 23 in first surface 15 in fluid communication with an end wall 25 located in the second surface 16 of the web 20. Each end wall 25 is provided with a multiplicity of relatively small openings 26. Each of the small openings 26 is sized and shaped so as to independently support an aqueous fluid meniscus. In addition, each opening 26 is so spaced relative to all adjacent openings 26 and to side wall 24 that any aqueous fluid meniscus which it supports will not contact any similar fluid menisci supported in any of the adjacent openings 26, nor will it contact side wall 24. When used as a breatheable backsheet in a disposable diaper, apertures 26 are preferably on the order of about 1 to about 5 mils (1 mil=0.001 inch) in diameter and exhibit relatively sharp shoulders at their exterior surface, i.e., the surface oriented toward the wearer's outer garments. The sharp shoulders help to increase the fluid contact angle, which further helps to support the fluid meniscus. In this regard, it is also preferred that the surface of the film exhibit the highest possible contact angle, i.e., the film surface should ideally be as hydrophobic as possible to help support the fluid menisci.

Figure 3:
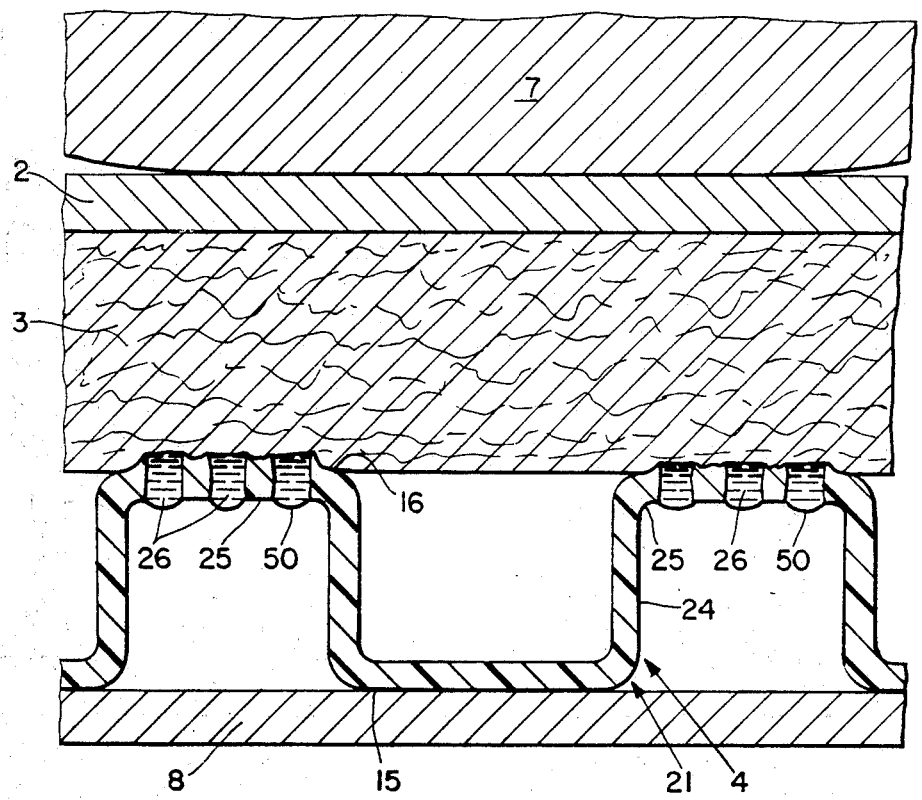
FIG. 3 is a greatly enlarged, simplified cross-sectional illustration of the web generally shown in FIG. 2 superposed upon the outermost surface of a moist absorbent substrate such as the absorbent pad of a disposable diaper, said structure being shown in an in use condition.

FIG. 3 is a greatly enlarged simplified cross-section of a moist segment of the disposable diaper generally shown in FIG. 1 in use, said diaper employing a breatheable backsheet 4 comprised of the material of web 20 shown in FIG. 2. In the condition illustrated in FIG. 3, body fluid such as urine has been transmitted through topsheet 2 and distributed throughout absorbent element 3. The wearer's body 7 is shown in contact with the uppermost surface of topsheet 2. Due to the effects of gravity, it is generally more difficult to restrain the passage of aqueous fluid through the backsheet when the absorbent bandage is generally in the orientation shown in FIG. 3. Accordingly, this orientation was chosen to ilustrate the advantages afforded by webs of the present invention.

The principal objective of employing a breatheable backsheet 4 on a disposable absorbent bandage such as diaper 1 is to permit fluids collected within absorbent element 3 to evaporate. This provides not only a cooling benefit, but also permits a greater total absorptive capacity, since liquid evaporated from the bandage 1 creates additional void space within absorbent element 3, which void space can be utilized to absorb newly deposited body fluids. However, in order for the wearer to appreciate the aforementioned benefits provided by breathability it is generally critical to prevent aqueous fluid transfer from the moist absorbent element 3 to the wearer's outer garment shown generally as 8 in FIG. 3.

In the condition illustrated in FIG. 3 little or no pressure is being exerted on the diaper 1 by compressive forces between the wearer's body 7 and the wearer's outer garment 8. This might be indicative of a situation in which the wearer is standing. Note that in FIG. 3, the relatively small apertures 26 in end walls 25 of debossments 21 are each supporting a liquid meniscus generally indicated as 50. These fluid menisci 50 prevent passage of the liquid by gravity through apertures 26 and onto the adjacent article of wearing apparel 8. So long as all of the fluid menisci 50 remain separated from one another and from the side wall 24 of debossments 21, fluid will not freely pass through apertures 26.

Furthermore, because the fluid menisci 50 are supported in end walls 25 of the debossments 21, they are physically isolated from contacting item of wearing apparel 8 by the overall caliper of web 20, i.e., the Z-direction separation between first surface 15 and second surface 16 of the web. Because contact between any of the fluid menisci 50 and article of wearing apparel 8 would result in transfer of fluid directly to the item of wearing apparel, it is extremely important that first surface 15 and second surface 16 of the web do not normally become coplanar with one another when subjected to compressive loadings typically experienced in use. It is also important that the overall caliper of web 20 be so related to the cross-sectional dimensions of debossments 21 that the item of wearing apparel 8 is not allowed to project significantly into the debossments 21 and thereby make contact with the fluid menisci 50 supported in apertures 26 of the end walls 25. This is particularly significant in situations where the item of wearing apparel 8 comprises a loosely woven or otherwise easily comfortable structure.

While the particular geometry selected will, of course, depend on the stiffness of the web material employed, for a typical material such as a one mil thick web of polyethylene an overall web caliper, i.e., the distance between surfaces 15 and 16 of web 20 is preferably at least about 1/5 to about ⅓ the minimum cross-sectional dimension of the debossment. This is based on the use of circular debossments 21 having a cross-sectional diameter of between about 10 mils and about 20 mils. For larger cross-sectional diameters and/or more compressible webs, it is generally desirable to increase the overall caliper of the web to minimize the chance of the second surface of the web containing the end walls of the debossments and the first surface of the web which contacts the wearer's outer garments becoming coplanar in use, as this would allow the aqueous fluid menisci supported in the end walls of the debossments to contact the item of wearing apparel 8.

Figure 4:
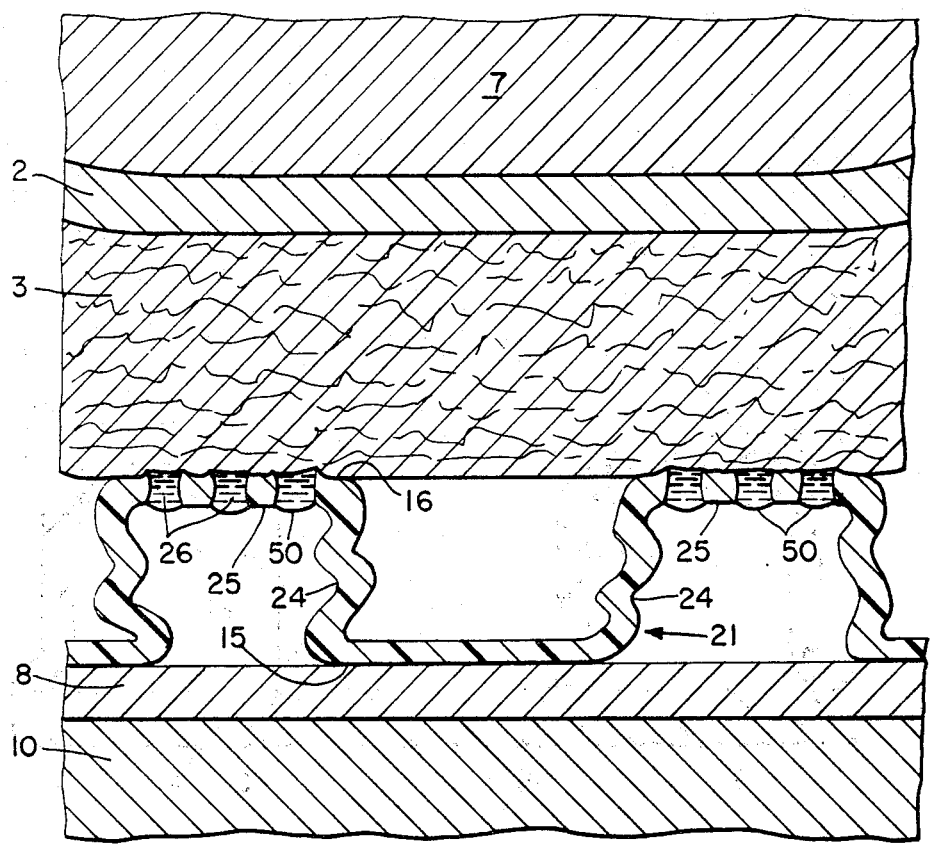
FIG. 4 is an illustration of the structure generally shown in FIG. 3 illustrating a typical response of the breathable web when typical compressive forces are exerted against the absorbent substrate and the wearer's outer garment.

FIG. 4 depicts the moist absorbent disposable diaper 1 shown in FIG. 3 under a typical compressive loading situation wherein compressive forces are applied to the diaper 1 by the wearer's body 7 and an external object 10. As can be observed from FIG. 4, sidewalls 24 of debossments 21 have undergone a degree of collapse. However, end walls 25 containing apertures 26 have still not become coplanar with the first surface of the web, nor have they made contact with item of wearing apparel 8. Accordingly, the fluid menisci 50 supported in apertures 26 are not contacted by item of wearing apparel 8. So long as the fluid menisci 50 do not become coplanar with first surface 15 of web 20, there is little chance for fluid transfer to occur directly from the moist absorbent element 3 to item of wearing apparel 8. (It is, of course, recognized that there will inevitably exist some possibility that isolated portions of the item of wearing apparel 8 may project substantially into one or more of the debossments 21 and thereby make contact with the fluid menisci 50 supported in apertures 26.)

Unlike the breatheable backsheet disclosed in the aforementioned commonly assigned patent to Sisson which employs conically shaped debossments, preferably with a single aperture provided at the tip of each cone, the substantially planar end walls 25 of the debossments 21 employed in a web of the present invention provide a multiplicity of apertures 26 sized, shaped and spaced so that each aperture will independently support an aqueous fluid meniscus without contacting either the side walls of the debossment or any other aqueous fluid meniscus supported by an aperture in the end wall.

Webs of the present invention are also distinct from the macroscopically expanded web structures disclosed in FIGS. 6, 6A, 6B and 7 of the aforementioned commonly assigned patent of Radel et al., since the apertures formed by the capillary networks of Radel et al. do not all originate in a single, substantially planar end wall. As will be pointed out hereinafter, the planar nature of the end wall of debossments 21 of webs of the present invention not only permits a greater open area in the web, thereby increasing the potential for evaporation, but also impacts significantly upon the web's ability to support an aqueous fluid meniscus.

As will be appreciated by those skilled in the art, debossments 21 need not be cylindrical in cross-section, as shown in FIG. 2, to function in the intended manner. The debossments 21 may be regular or irregular in shape, and will still function in the intended manner, provided they establish a comparable contact angle with the aqueous liquid, and further provided they are of the proper size range. If, for purposes of this specification, the cross-sectional shape of the debossment is defined by a major axis which coincides with the maximum cross-sectional dimension of the debossment and a minor axis which coincides with the minimum cross-sectional dimension of the debossment, as measured perpendicularly at the same point along the longitudinal axis of the debossment, the minor axis will normally be controlling in preventing the wearer's apparel from entering the debossment and contacting the end wall 25 thereof.

In order to maximize the breathability of webs of the present invention, it is generally desirable that the debossments occupy as large a percentage of the web's area as is feasible, consistent with the ability to resist becoming coplanar under compressive loads tyically experienced in use. (These loads are normally on the order of about one pound per square inch or less when used in the context of a disposable diaper). In general, the greater the open area of the end walls of the debossments, the greater will be the opportunity for evaporation to occur from the liquid menisci supported in the apertures. To maximize the evaporative benefit, it is generally desirable to size apertures 26 as large as is practical, consistent with the requirement that they support an aqueous fluid meniscus, and to space the apertures 26 relative to one another and to the side wall 24 of the debossment 21 so that the menisci supported in the apertures of any given end wall do not contact one another or the sidewall of the debossment.

As will be appreciated by those skilled in the art, it is not necessary that the entire surface of a web be breatheable. Selective breatheability can, if desired, be provided in isolated portions of the web. For example, only the cuff areas or the waistband areas for a breatheable backsheet for a disposable diaper might be made breatheable, since in use compressive loadings may be lower in those areas. Furthermore, it may, in certain instances, prove desirable to employ multiple, non-nesting layers of a web of the present invention to enhance the fluid isolation effect provided by webs of the present invention without negating vapor permeability of the multiple layers. In such situations, orientation of the web surfaces may be similar or dissimilar, as desired.

To provide adequate physical isolation and hence prevention of direct fluid transmission between the end walls of the debossments and the adjacent item of wearing apparel, the physical separation between the first and second surfaces of the breatheable web, i.e., the perpendicular distance between surfaces 15 and 16 of web 20, is preferably at least about 1/5 to about ⅓ the minimum cross-sectional dimension of the debossment in question. As will be appreciated from an inspection of FIG. 2, the separation between surfaces 15 and 16 is established by the overall length of debossment side walls 24. In general, the maximum side wall length can be on the order of about half the major axis dimension of the largest debossment, as measured perpendicular to the longitudinal axis of the debossment. This is due to fact that if the effects of material thinning during the macroscopic expansion process are ignored, the material comprising the debossment 21 is that which initially occupied the area framed by aperture 23 prior to macroscopic expansion of the web. However, as will be described in greater detail in the latter portions of this specification, the precise Z-direction separation between the first and second surfaces of webs of the present invention is normally determined by the configuration of the forming structure on which the web is macroscopically expanded.

Figure 5:
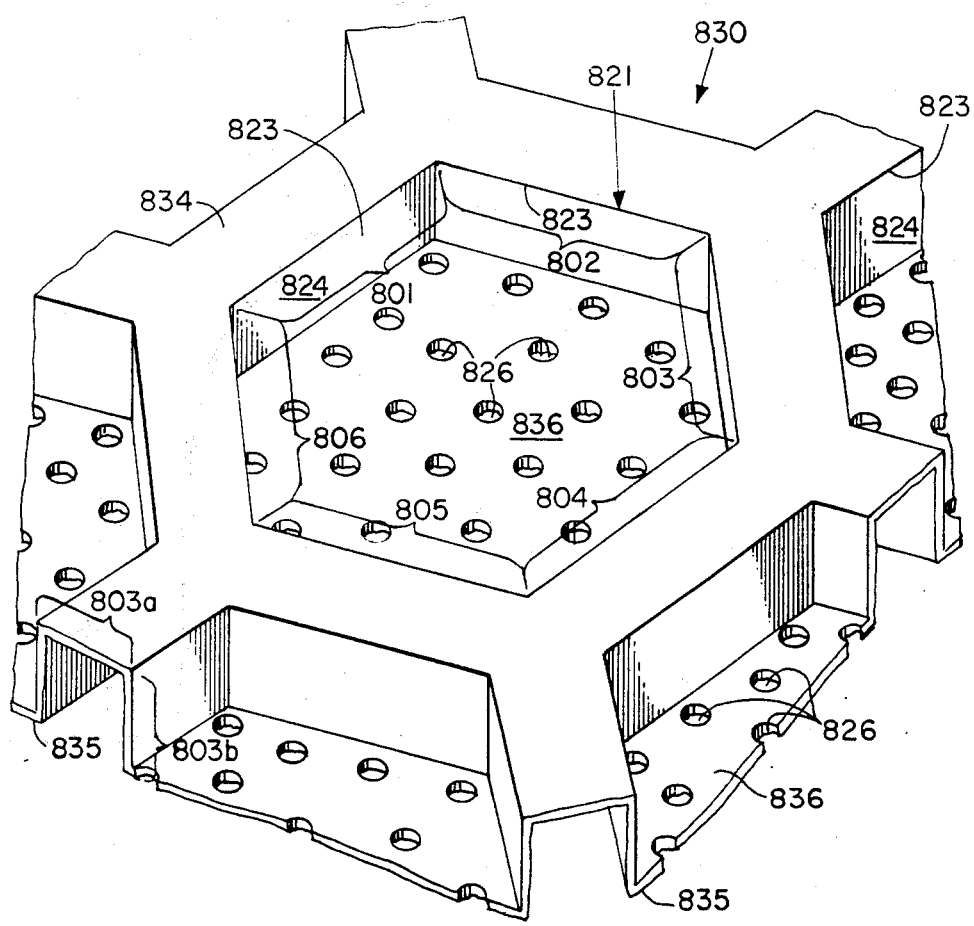
FIG. 5 is a greatly enlarged perspective view of a segment of an alternative apertured, macroscopically expanded three-dimensional polymeric web suitable for use as a backsheet in a disposable diaper such as that shown in FIG. 1.

FIG. 5 depicts an alternative embodiment of a macroscopically expanded three-dimensional polymeric web 830 of the present invention. The web 830 depicted in FIG. 5 is a fiber-like web similar to the one generally illustrated and described in connection with FIG. 6D of commonly assigned U.S. Pat. No. 4,342,314 issued to Radel et al. on Aug. 3, 1982 and incorporated herein by reference. However, the FIG. 6D web embodiment of Radel et al. does not exhibit aperturing in the end walls of its debossments, while web embodiment 830 of the present invention exhibits a multiplicity of apertures, e.g., apertures 826 in end walls 836 of debossments 821. Apertures 823 in the first surface 834 of the web are each formed by a multiplicity of intersecting fiber-like elements of generally U-shaped cross-section, e.g., fiber-like elements 801, 802, 803, 804, 805 and 806, interconnected to one another in the first surface 834 of the web. Each fiber-like element comprises a base portion, e.g., base portion 803a, located in first surface 834. Each base portion has a side wall portion, e.g., side wall portions 803b, attached to each edge thereof. The side wall portions extend generally in the direction of the second surface 835 of the web. The intersecting side wall portions of the fiber-like elements are connected to one another intermediate the first and second surfaces of the web, and terminate substantially concurrently with one another in the second surface 835 of the web to form end walls 836. The side wall portions of the fiber-like elements may be oriented substantially perpendicular to the base portion of the fiber-like elements or they may be angled with respect to the base portion, thereby producing end walls 836 in the second surface 835 of the web which are smaller in size than the apertures 823 in the first surface 834 of the web. In the latter case each resultant debossment 821 is of decreasing cross-section in the direction of the second surface.

As with the web embodiment 20 shown in FIG. 2, the end walls 836 of debossments 821 of web 830 contain a multiplicity of relatively small apertures 826, said apertures being sized, shaped and spaced so that they will each independently support an aqueous fluid meniscus. Thus, web embodiment 830 permits evaporation of absorbed aqueous fluids to occur through the small apertures 826 in debossment end walls 836, but resists the transmission of aqueous fluid through the small apertures either by gravity or by physical contact with the wearer's apparel.

Apertured, macroscopically expanded, three-dimensional polymeric web embodiments of the type generally shown in FIGS. 2 and 5 can be made generally in accordance with the teachings of the FIG. 10 embodiment of the commonly assigned U.S. patent application of John J. Curro, James C. Baird, Donald L. Gerth, George M. Vernon and E. Kelly Linman, entitled MULTI-PHASE PROCESS FOR DEBOSSING AND PERFORTING A POLYMERIC WEB TO COINCIDE WITH THE IMAGE OF ONE OR MORE THREE-DIMENSIONAL FORMING STRUCTURES, Ser. No. 740,145, said patent application being concurrently filed herewith and hereby incorporated herein by reference.

Figure 6:
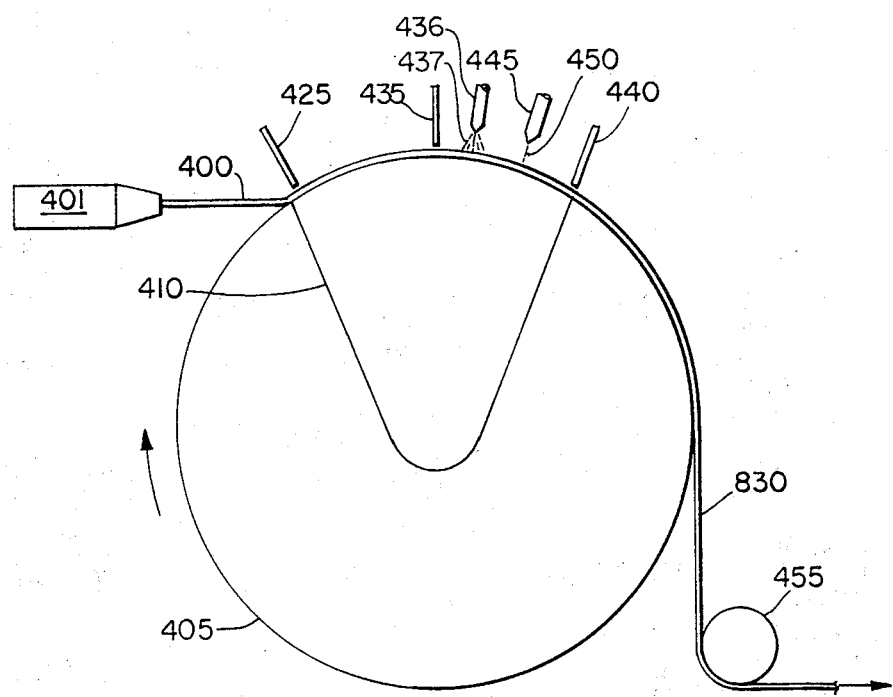
FIG. 6 is a simplified schematic illustration of a preferred process which may be utilized to produce apertured, macroscopically expanded, three-dimensional polymeric webs of the present invention.

A particularly preferred process for producing an apertured, macroscopically expanded, three-dimensional, breatheable polymeric web of the present invention is schematically illustrated in simplified form in FIG. 6 of the present specification. Basically, the preferred process illustrated in FIG. 6 is initiated by extruding a polymeric resin melt 400 from a conventional extruder 401 onto a three-dimensional forming structure made in a manner somewhat similar to that taught in commonly assigned U.S. Pat. No. 4,395,215 issued to Bishop on July 26, 1983 and hereby incorporated herein by reference.

Figure 7:
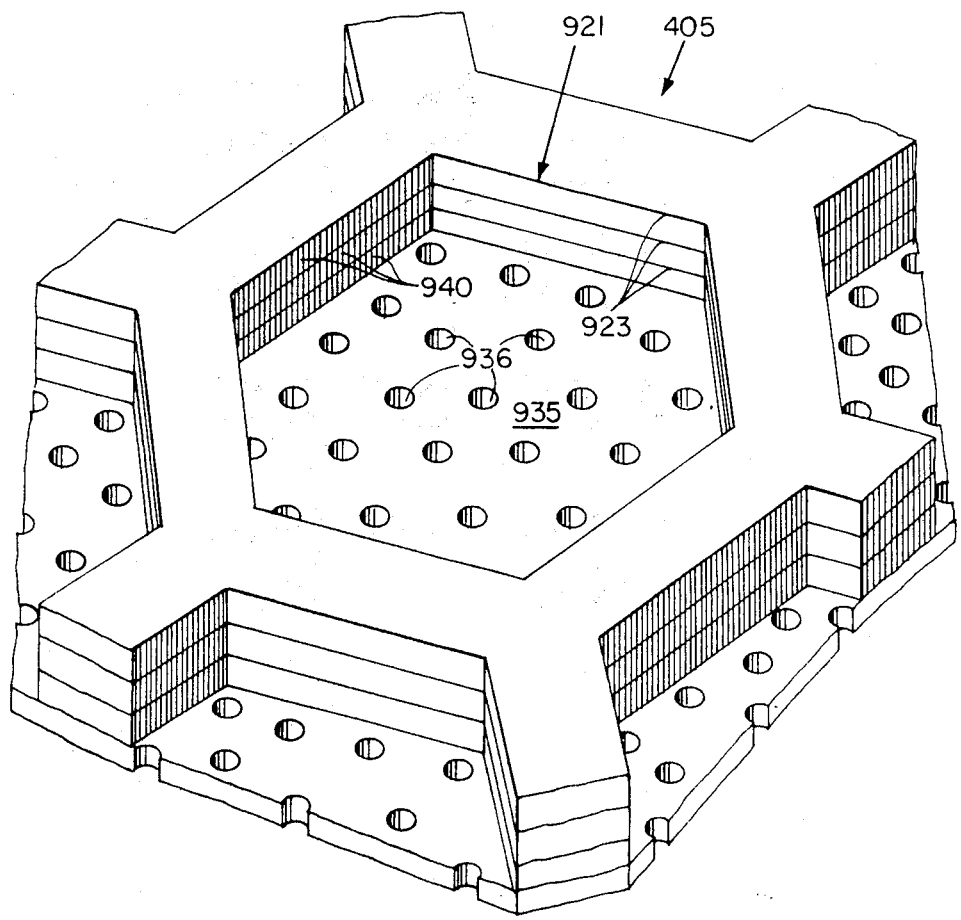
FIG. 7 is a greatly enlarged perspective illustration of a segment of a forming structure suitable for producing a polymeric web such as that shown in FIG. 5 using a process such as that schematically illustrated in FIG. 6.

The three-dimensional cylindrical forming structure 405, a greatly enlarged segment of which is shown in FIG. 7, traverses a fluid pressure differential zone preferably comprising a stationary vacuum chamber 410. Stationary baffles 425 and 440 are preferably provided at the leading and trailing edges, respectively of vacuum chamber 410. The subatmospheric pressure existing within vacuum chamber 410 causes the heated polymeric melt 400 to undergo macroscopic expansion and three-dimensionally conform to the surface of the forming structure 405 to form debossments corresponding to the macroscopic cross-section cavities contained in the forming structure. Because of the relatively small size desired for the apertures in the end walls of the debossments, rupture of the macroscopically expanded polymeric melt 400 does not normally occur during the initial application of suction by vacuum chamber 410. Rather, the initial phase of the process serves primarily to deeply draw and fully conform the polymeric melt 400 to the macroscopic profile of the forming structure 405.

To ensure that the macroscopically expanded, three-dimensional geometry imparted to the melt by the suction is not lost due to spring-back of the melt upon removal from the vacuum chamber, it is preferable to lower the temperature of the melt sufficiently that its overall caliper is not appreciably reduced when it clears the trailing edge of the vacuum chamber 410. In the embodiment illustrated in FIG. 6, some of the required cooling occurs by means of exposure to the surrounding atmosphere while the web is on the forming structure 405 and subject to the influence of vacuum chamber 410. However, the cooling operation is preferably assisted by applying a low pressure, i.e., less than about 50 psig, cooling water spray 436 issuing from nozzle 435 adjacent the trailing edge of stationary baffle 435. The web is then passed beneath high pressure, i.e., about 400 psig or greater, liquid jet nozzle 45 which impinges a jet of liquid, preferably water, 450 against the outermost surface of the web and causes aperturing of those portions of the macroscopically expanded web which coincide with the small apertures 936 contained in the forming structure 405. Because of the high pressure of the water jet, particularly when compared to the relatively small fluid pressure differential forces applied to the web by vacuum chamber 410, the web is fully conformed and fully apertured in the image of the forming structure. This provides deeply drawn debossments 821 having end walls 836 containing a multiplicity of relatively small apertures 826 coinciding with apertures 936 in forming structure 405.

If the thickness of the film comprising web 830 is ignored, the apertures 826 in the end walls 836 of debossments 821 are substantially the same in size and shape as apertures 936 in the lowermost lamina 935 of forming structure 405.

As can be seen in FIG. 6, the water used to produce the small apertures 826 in web 830 is preferably collected inside vacuum chamber 410 and is recycled by means of suitable separating apparatus (not shown) to a high pressure pump (not shown) which redelivers the water under high pressure to nozzle 445.

The latter phase of the forming process disclosed in FIG. 6 is generally similar to that described in the commonly assigned co-pending patent application of John J. Curro, Allen J. Trusty and George M. Vernon entitled FORMED MATERIAL PRODUCED BY SOLID-STATE FORMATION WITH A HIGH PRESSURE LIQUID STREAM, Ser. No, 580,911, filed Feb. 16, 1984 and hereby incorporated herein by reference.

The resultant apertured, macroscopically expanded, three-dimensional breatheable polymeric web 830 is preferably removed from the surface of the forming structure 405 by feeding it about idler roller 455, after which it may be directed to further processing operations (not shown) or to a suitable rewind station (not shown), as desired.

As pointed out earlier herein, FIG. 7 discloses a particularly preferred forming structure 405 which may be employed to produce a web of the type generally shown in FIG. 5. Forming structure 405 is preferably constructed from laminar layers generally in accordance with the teachings of the aforementioned commonly assigned patents to Radel et al. (U.S. Pat. No. 4,342,314) and Bishop (U.S. Pat. No. 4,395,215), both of said patents being incorporated herein by reference. FIG. 7 of the Bishop patent discloses a greatly enlarged exploded segment of a forming structure for selectively aperturing a macroscopically expanded, three-dimensional polymeric web. As can be seen from FIG. 7 of the aforementioned Bishop patent, a portion of one of the laminar layers is comprised of a finely apertured material. Where aperturing of the polymeric web is desired, that particular layer of the Bishop forming structure is macroscopically apertured to coincide with the overall pattern exhibited by the forming structure. Those portions of the polymeric web which come in contact with the finely apertured portion of the lamina which has not been made to coincide with the macroscopically apertured portion of the forming structure of Bishop provide sufficient support to the web that when a vacuum forming process is employed to macroscopically deboss and macroscopically aperture the web, fine scale aperturing does not normally occur in the areas coinciding with the very fine holes of the selectively apertured layer. The laminate forming structure 405 shown in FIG. 7 of the present application differs from that shown in FIG. 7 of the Bishop patent in that a pattern of relatively small apertures 936 is provided throughout the forming structure in those areas intended to coincide with the end walls 826 of the debossments 821 contained in web 830. The remainder of the lamina 940 used to create a forming structure of the present invention contain identical patterns of apertures 923. When superposed in register with one another, bonded, and converted to tubular form, laminate forming structures of the present invention serve to form apertures 823, side walls 824, and end walls 836 containing apertures 826 when a process such as that generally illustrated in FIG. 6 is carried out.

Figure 8:
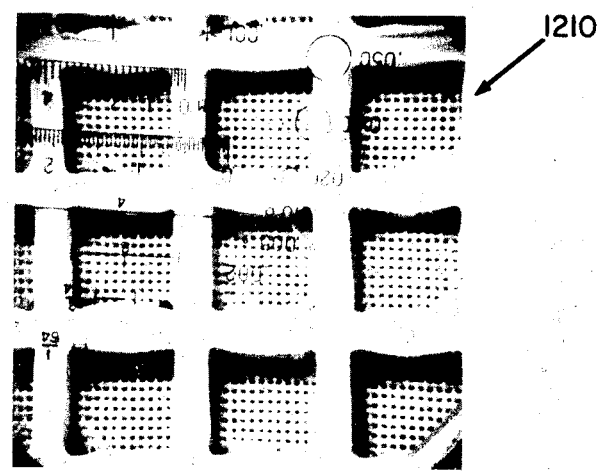
FIG. 8 is a greatly enlarged photograph of a sample web of the present invention, said sample web being viewed from its garment contacting side.

A greatly enlarged plan view photograph of a sample web 1210 of the present invention is shown in FIG. 8. The details of this web and the conditions under which it was produced are more fully set forth in Example III of the aforementioned commonly assigned U.S. patent application of John J. Curro, James C. Baird, Donald L. Gerth, George M. Vernon and E. Kelly Linman, entitled MULTI-PHASE PROCESS FOR DEBOSSING AND PERFORATING A POLYMERIC WEB TO COINCIDE WITH THE IMAGE OF ONE OR MORE THREE-DIMENSIONAL FORMING STRUCTURES, Ser. No. 740,145, concurrently filed herewith and incorporated herein by reference is shown in FIG. 8. This view is taken from the garment contacting surface of the web.

Although the present invention has been described in the context of a backsheet for a disposable diaper, it is of course recognized that the present invention may also be practiced to advantage in other environments where resistance to liquid transmission, vapor permeability and resistance to compression are all desired characteristics.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A macroscopically expanded, resilient three-dimensional polymeric web having first and second surfaces located in substantially parallel planes which are remote from one another, said web including a multiplicity of debossments of macroscopic cross-section, each of said macroscopic cross-section debossments originating as an aperture in said first surface of said web and having a continuously interconnected side wall extending in the direction of said second surface of said web, said continuously interconnected side wall terminating to form an end wall located in said second surface of said web, said end wall including a multiplicity of apertures in said second surface of said web, said apertures in said second surface of said web being smaller in size than the corresponding macroscopic aperture in said first surface of said web, said web exhibiting sufficient resistance to compression that said first and said second surfaces of said web do not become coplanar with one another when said web is subjected to a compressive loading of about one pound per square inch, and a degree of resilience sufficient to return substantially to its undeformed condition when said compressive load is removed from said web.

2. The macroscopically expanded, resilient web of claim 1, wherein each of said apertures in the end wall of each of said macroscopic cross-section debossments is of a size capable of independently supporting an aqueous fluid meniscus, each of said apertures in said end wall being so spaced relative to all adjacent apertures in said end wall that the aqueous fluid meniscus in any particular aperture will not contact a similar aqueous fluid meniscus in any adjacent aperture.

3. The web of claim 2, wherein said apertures in said end wall are cylindrical in shape and the maximum dimension of each of said apertures in said end wall is approximately 5 mils.

4. The web of claim 2, wherein said first and second surfaces of said web are separated from one another by an overall distance sufficient to prevent entry by any aqueous fluid menisci supported in the apertures included in the end walls of said macroscopic debossments into the plane of said first surface of said web when said web is subjected to a compressive loading of about one pound per square inch.

5. The web of claim 4, wherein said first and second surfaces of said web are separated from one another by a distance of at least about 1/5 of the minimum cross-sectional dimension of said macroscopic debossments.

6. The web of claim 4, wherein said first and second surfaces of said web are separated from one another by a distance of at least about ⅓ of the minimum cross-sectional dimension of said macroscopic debossments.

7. The web of claim 6, wherein said polymeric web is comprised of polyethylene.

8. The web of claim 1, wherein substantially all of said macroscopic cross-section debossments are of substantially the same size.

9. The web of claim 1, wherein substantially all of said macroscopic cross-section debossments are of substantially the same shape.

10. The web of claim 2, wherein substantially all of said apertures in said end wall are of substantially the same size and shape.

11. An absorbent device comprising:
(a) a liquid-pervious wearer contacting topsheet;
(b) a liquid absorbent element secured beneath said liquid-pervious topsheet; and
(c) a breatheable backsheet which is vapor-pervious, but resistant to the transmission of liquid, secured adjacent the surface of said absorbent element opposite said topsheet, said backsheet comprising a macroscopically expanded, resilient three-dimensional polymeric web having first and second surfaces located in substantially parallel planes which are remote from one another, said web including a multiplicity of debossments of macroscopic cross-section, each of said macroscopic cross-section debossments originating as an aperture in said first surface of said web and having a continuously interconnected side wall extending in the direction of said second surface of said web, said continuously interconnected side wall terminating to form an end wall located in said second surface of said web, said end wall including a multiplicity of apertures in said second surface of said web, said apertures in said second surface of said web being smaller in size than the corresponding macroscopic aperture in said first surface of said web, said web exhibiting sufficient resistance to compression that said first and said second surfaces of said web do not become coplanar with one another when said web is subjected to a compressive loading of about one pound per square inch, and a degree of resilience sufficient to return substantially to its undeformed condition when said compressive load is removed from said web, said web being oriented so that its second surface is in contact with said liquid absorbent element.

12. The absorbent device of claim 11, wherein said backsheet overlies at least a portion of said wearer contacting topsheet.

* * * * *

UNITED STATES PATENT AND TRADEMARK OFFICE
CERTIFICATE OF CORRECTION

PATENT NO. : 4,591,523

DATED : May 27, 1986

INVENTOR(S) : HUGH A. THOMPSON

It is certified that error appears in the above-identified patent and that said Letters Patent is hereby corrected as shown below:

Column 1, line 59, "It" should read -- In --.

Column 1, line 64, "absorbent" should read -- absorbed --.

Column 2, line 62, "aperture" should read -- apertured --.

Column 3, line 15, "extending" should read -- exhibiting --.

Column 3, line 30, "improvement" should read -- improved --.

Column 6, line 35, "ilustrate" should read -- illustrate --.

Column 7, line 15, "comfortable" should read -- conformable --.

Column 8, line 33, "tyically" should read -- typically --.

Column 10, line 7, "PERFORTING" should read -- PERFORATING --.

Signed and Sealed this

Twenty-sixth Day of August 1986

[SEAL]

Attest:

DONALD J. QUIGG

Attesting Officer

Commissioner of Patents and Trademarks